United States Patent [19]

King

[11] Patent Number: 4,727,208

[45] Date of Patent: Feb. 23, 1988

[54] OXIDATIVE COUPLING WITH METHYL-SUBSTITUTED BENZENES

[75] Inventor: Stanley S. T. King, Midland, Mich.

[73] Assignee: The Dow Chemical Company, Midland, Mich.

[21] Appl. No.: 906,472

[22] Filed: Sep. 12, 1986

[51] Int. Cl.4 ............................................... C07C 2/72
[52] U.S. Cl. ..................................... 585/428; 585/426
[58] Field of Search ................................ 585/426, 428

[56] References Cited

U.S. PATENT DOCUMENTS

| 2,904,580 | 9/1957 | Idol, Jr. | |
|---|---|---|---|
| 4,091,044 | 5/1978 | Li | 585/428 |
| 4,254,293 | 3/1981 | Tremont | 585/426 |
| 4,268,704 | 5/1981 | Tremont | 585/426 |
| 4,390,728 | 6/1983 | Daniel | |
| 4,517,397 | 5/1985 | Terauchi et al. | 585/428 |

FOREIGN PATENT DOCUMENTS

| 24323 | 2/1982 | Japan . |
| 121238 | 7/1983 | Japan . |

OTHER PUBLICATIONS

*Chem. Abs.*, 97(15):126,725m, abstracting Madhock et al.
*Indian J. Technol.*, 20(50), 184–89 (1982).
Andersson, J. Catal., 98, 138 (1986).

*Primary Examiner*—Curtis R. Davis

[57] ABSTRACT

The invention, in one aspect, is a process for preparing a (methyl-substituted)diphenyl methane by coupling at least (including benzene) a methyl-substituted benzene into the (methyl-substituted)diphenyl methane comprising contacting at least the methyl-substituted benzene with a solid heterogeneous reactant-catalyst having labile oxygen under conditions whereby the (methyl-substituted)diphenyl methane is prepared. For example, using molybdenum trioxide or vanadium pentoxide, toluene can be coupled in the vapor or liquid phase to prepare (2-methylphenyl)phenylmethane. By-product formation, especially formation of carbon dioxide, can be very low.

11 Claims, No Drawings

OXIDATIVE COUPLING WITH METHYL-SUBSTITUTED BENZENES

FIELD

This invention concerns coupled aromatic compounds, with a process for their preparation.

BACKGROUND

The catalytic oxidation of toluene can produce benzaldehyde and benzoic acid. See, for example, Daniel, U.S. Pat. No. 4,390,728 (1983); *Chem. Abs.*, 97(15):126,725m, abstracting Madhock et al., *Indian J. Technol.*, 20(5), 184–89 (1982); Andersson, *J. Catal.*, 98, 138 (1986).

Anthraquinone has been allegedly prepared by the use of diluted toluene in air (1.2 percent). See, for example, Japan Kokai Nos. 1982-24323 and 1983-121238. Such known processes to prepare anthraquinone by direct toluene oxidation can be generally inefficient. Loss of valuable reactant materials through complete combustion to carbon dioxide can be particularly problematical.

SUMMARY

The invention is a process for preparing a (methyl-substituted)diphenyl methane by coupling at least a methyl-substituted benzene into the (methyl-substituted)diphenyl methane comprising contacting at least the methyl-substituted benzene with a solid heterogeneous reactant-catalyst having labile oxygen under conditions whereby the (methyl-substituted)diphenyl methane is prepared. The process is highly efficient. By-product formation, and loss of reactants such as by carbon dioxide formation, is greatly minimized. The process can be carried out in either vapor or liquid phases.

The process prepares useful products. The (methyl-substituted)diphenyl methanes are generally useful as chemical intermediates for preparing anthraquinones which are generally useful, for example, as dye intermediates and pulping catalyst.

ILLUSTRATIVE EMBODIMENTS

In general, the methyl-substituted benzenes include compounds represented by the formula

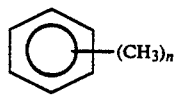
(I)

wherein n is an integer from 1 to 6, preferably from 1 to 5, more preferably from 1 to 3, most preferably 1 or 2. Especially preferred of the methyl-substituted benzenes are toluene and/or ortho-xylene. At least one of the methyl-substituted benzenes to be coupled into the methyl-substituted diphenyl methanes must have at least one hydrogen available on the benzene ring.

Benzene itself can be employed as reactant for coupling by the process of the invention, so long as the methyl-substituted benzene is also present as reactant. Hence, "at least" may modify methyl-substituted benzene. However, the resulting (methyl-substituted)diphenyl methane is, of course, to a larger extent, a mixture of coupled products, one of which can be diphenyl methane.

In general, the (methyl-substituted)diphenyl methanes are coupled compounds represented by the formula

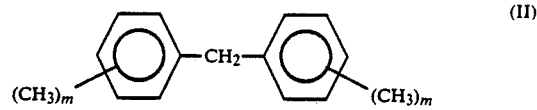
(II)

wherein m is separately at each occurrence an integer from zero to 5, preferably zero to 4, more preferably from zero to 2, most preferably zero to one, and especially one m value is zero while the other m value is one. Preferably, at least one methyl group(s) of the compounds of the formula (II) is (are) in a position ortho to the coupled methylene group such as found, for example, in (2-methylphenyl)phenylmethane.

The reactant-catalyst employed in the process of the invention is a heterogeneous solid. The solid heterogeneous reactant-catalyst contains labile oxygen. The term "reactant-cataylst" means a substance which generally can be considered both or either a reactant and/or a catalyst. As a reactant, the heterogeneous substance generally supplies the labile oxygen to the remaining components of the reaction medium, itself thus losing the oxygen. As a catalyst, the heterogeneous substance generally can be regenerated in the catalytic cycle. The term "labile", which modifies oxygen, means able to be supplied to the remaining components of the reaction medium from the heterogeneous reactant-catalyst. The reactant-catalyst the invention may be supported with a support such as, for example, silica or alumina and so forth and the like.

For example, toluene reacts with oxygen in metal oxides such as, in general, $V_2O_5$, $MoO_3$, bismuthmolybdate-containing catalysts and heteropolyoxometalates such as, for example, heteropoly(cage)molybdates and/or tungstates, without gas phase oxygen to form (2-methylphenyl)phenylmethane at 150° C.–500° C., and thus, substances such as these are solid heterogeneous reactant-catalysts having labile oxygen under these general conditions. Preferably, the bismuthmolybdate-containing catalyst is such as disclosed by Idol, Jr., U.S. Pat. No. 2,904,580 (1957) (incorporated herein by reference), which is termed "Type SA" (i.e., Sohio Type A) or more generically termed, a bismuth phosphomolybdate catalyst. The most preferred species of the solid heterogeneous reactant-catalysts are, in general, $MoO_3$ and $V_2O_5$.

In general, the temperatures of the process are elevated. Elevated temperatures include those such as from 50° C. to 700° C. Preferred elevated temperatures generally range from 100° C. to 500° C. More preferable elevated temperatures for the vapor phase process are generally from 300° C. to about 450° C. Elevated temperatures of the process carried out in the liquid phase may be generally lower than those of the process carried out in the vapor phase. Preferred elevated temperatures can vary with the specific solid heterogeneous reactant-catalyst employed such as illustrated for the vapor phase process by the most preferred temperatures of the following table.

| Catalyst | General Temperature |
| --- | --- |
| Generally, V$_2$O$_5$ | 350° C. |
| Generally, MoO$_3$ or Type SA | 400° C. |

In general, the liquid phase process is carried out neat, and the vapor phase process can be carried out neat or with an inert gaseous diluent present as a so-called carrier gas. Preferred carrier gases include nitrogen, helium and argon. Unreacted methyl-substituted benzenes are preferably recycled as a reactant.

To couple the methyl-substituted benzenes into the (methyl-substituted)diphenyl methanes, at least the methyl-substituted benzenes are brought into contact with the solid heterogeneous reactant-catalyst having labile oxygen. Oxygen such as gaseous oxygen is preferably absent during the coupling. The (methyl-substituted)diphenyl methanes are prepared, and the available labile oxygen of the solid heterogeneous reactant-catalyst depletes.

Generally, subsequent to the depletion of the labile oxygen of the solid heterogeneous reactant-catalyst, the reactant-catalyst is regenerated by contact with oxygen to provide available labile oxygen to the solid heterogeneous reactant-catalyst. The regenerative contact is generally with oxygen, for example, gaseous oxygen, including gaseous oxygen dissolved in at least one carrier gas, for example, as in air. The regenerative contact with the oxygen need not be direct as in air contacting the same general site of the prior contacting of at least the methyl-substituted benzenes with the now depleted solid heterogeneous reactant-catalyst itself, but can be by a more circuitous route such as by diffusion through a solid such as by air contacting the "back side" of the solid heterogeneous reactant-catalyst or membrane upon which it can be supported, which is not the same general site as of the prior, or even ongoing, contact of the methyl-substituted benzene(s) with the solid heterogeneous reactant-catalyst.

Preferably, the replenishing of the labile oxygen is by air. Multiple alternating beds of solid heterogeneous reactant-catalyst at various stages of coupling and depletion of labile oxygen and its regeneration can be employed.

The (methyl-substituted)diphenyl methanes can be recovered, and/or purified if desired, by known procedures. Preferred are low temperature vapor traps.

Conversion herein is the molar percent of the organic reactant(s) which is (are) changed into any and all product(s). The conversion can vary widely depending on operating conditions, and can typically be from about one to 80 mole percent. Selectivity herein is the molar percent of a specific product(s) which is (are) prepared, based upon moles of the organic reactant(s) which is (are) converted, that is, based upon the conversion. For example, if 10 moles of the organic reactant toluene are employed and 5 moles of the toluene are changed into any and all product(s), then the conversion is 50 percent. If, of the 5 moles of the toluene which are converted, one mole of the toluene appears as 7 moles of carbon dioxide, then selectivity to carbon dioxide is 20 percent. If, of the 5 moles of the toluene which are converted, 3 moles of the toluene appears as 1.5 moles of a (methylphenyl)phenylmethane, then selectivity to (methylphenyl)phenylmethane(s) is 60 percent. Preferably, selectivity to the (methyl-substituted)diphenyl methane is at least 20 percent, more preferably at least 40 percent and most preferably at least 60 percent. Concurrently thus, by-product formation can be correspondingly low. Especially notable is the extremely low level of formation of the by-product carbon dioxide which is preferably formed at the selectivity of at most about 65 percent, more preferably at most 30 percent and most preferably at most 10 percent.

SPECIFIC EMBODIMENTS

The following examples further illustrate the invention. Parts, percentages and ratios are by weight unless otherwise specified.

EXAMPLE 1

Vapor Phase

MoO$_3$ powder (0.109 g) is heated in a quartz tube to 400° C. with helium purge at a constant rate of 30 cc/min. Toluene is introduced into the reactor in the helium stream at a rate of 50 μl/min. The reaction products are analyzed by an on-line gas chromatograph and an infrared spectrometer, and 70 percent of the product is two methyldiphenylmethane (MDPM) isomers. The ratio of (2-methylphenyl)phenylmethane to (4-methylphenyl)phenylmethane is 8:2. The other 30 percent contains benzaldehyde, methylbenzophenones, anthraquinone and a small amount of carbon dioxide. The catalyst deactivates in 5 minutes due to the depletion of the oxygen. 0.47 mg of MDPM isomers are obtained. Upon purging of the toluene from the reactor, air is used to regenerate the catalyst. A total of 130 micromoles of carbon dioxide is collected from the combustion of coke on catalyst. The toluene selectivities to MDPM, coke and others such as benzaldehyde, benzoic acid and benzophenone are 38 percent, 62 percent and 11 percent, respectively.

EXAMPLE 2

Vapor Phase

Similarly to the procedure of Example 1, ortho-xylene is employed as the organic reactant. Gas chromatography analysis shows production of (methyl-substituted)diphenyl methanes.

EXAMPLE 3

Liquid Phase

A sample of 0.57 g of toluene is heated with 0.52 g of V$_2$O$_5$ at 200° C. in a small stainless steel container for 2 hours. One percent of the toluene is converted into MDPM, anthraquinone, benzaldehyde and carbon dioxide at respective selectivities of 70.3 percent, 18.7 percent, 18.2 percent and 2.8 percent. The (2-methylphenyl) to (4-methylphenyl) isomer ratio of the MDPM is 70:30.

I claim:

1. A process for preparing a (methyl-substituted)-diphenyl methane by coupling at least a methyl-substituted benzene into the (methyl-substituted)diphenyl methane comprising contacting at least the methyl-substituted benzene with a solid heterogeneous reactant-catalyst having labile oxygen under conditions whereby the (methyl-substituted)diphenyl methane is prepared, said solid heterogeneous reactant-catalyst having labile oxygen being selected from the group consisting of a vanadium oxide, a molybdenum oxide, and a bismuth-molybdate-containing catalyst.

2. The process of claim 1 wherein the temperature is from about 50° C. to about 700° C., and selectivity to carbon dioxide is at most about 65 percent.

3. The process of claim 2 wherein the methyl-substituted benzene is selected from the group consisting of toluene and ortho-xylene.

4. The process of claim 3 wherein the methyl-substituted benzene is toluene.

5. The process of claim 3 wherein the methyl-substituted benzene is ortho-xylene.

6. The process of claim 3 wherein the (methyl-substituted)diphenyl methane is prepared in a selectivity of at least 20 percent.

7. The process of claim 1 which is carried out in the vapor phase.

8. The process of claim 7 wherein the solid heterogeneous reactant-catalyst is selected from the group consisting of molybdenum trioxide and vanadium pentoxide.

9. The process of claim 1 which is carried out in the liquid phase.

10. The process of claim 9 wherein the solid heterogeneous reactant-catalyst is selected from the group consisting of molybdenum trioxide and vanadium pentoxide.

11. A process for preparing a (methyl-substituted)diphenyl methane by coupling at least a methyl-substituted benzene into the (methyl-substituted)diphenyl methane comprising contacting at least the methyl-substituted benzene with molybdenum trioxide or vanadium pentoxide under conditions whereby the (methyl-substituted)diphenyl methane is prepared.

* * * * *